United States Patent [19]

Riceberg

[11] 4,350,659

[45] Sep. 21, 1982

[54] STABILIZATION OF SENSITIVE BIOLOGICALLY ACTIVE INTERMEDIATE METABOLITES SUCH AS FOLIC ACID DERIVATIVES

[75] Inventor: Louis J. Riceberg, Needham, Mass.

[73] Assignee: Corning Glass Works, Corning, N.Y.

[21] Appl. No.: 288,463

[22] Filed: Jul. 30, 1981

[51] Int. Cl.³ .................... G01N 33/68; G01N 1/00
[52] U.S. Cl. ................................. 422/61; 23/230 B; 424/1; 435/188; 544/261
[58] Field of Search ................ 435/188; 23/230 B; 422/61

[56] References Cited

U.S. PATENT DOCUMENTS

| | | | |
|---|---|---|---|
| 3,879,262 | 4/1975 | Schuurs | 435/188 X |
| 3,928,566 | 12/1975 | Briggs | 424/94 |
| 4,136,159 | 1/1979 | Stone | 23/230 B X |
| 4,146,602 | 3/1979 | Gutcho et al. | 424/1 |
| 4,188,465 | 2/1980 | Schneider | 435/188 X |
| 4,228,240 | 10/1980 | Dawson | 435/188 |
| 4,244,943 | 1/1981 | Yamahira | 435/188 X |
| 4,258,030 | 3/1981 | Sasaki | 435/188 X |
| 4,279,859 | 7/1981 | Gutcho | 422/61 |
| 4,298,735 | 11/1981 | Farina | 23/230 B X |
| 4,300,907 | 11/1981 | Mansbach | 422/61 X |
| 4,314,988 | 2/1982 | Farina | 23/230 B |

*Primary Examiner*—Sidney Marantz
*Attorney, Agent, or Firm*—William E. Maycock

[57] ABSTRACT

A sensitive intermediate metabolite such as a folic acid derivative or analog is stabilized by complexing it with a complementary binder or receptor such as a protein and then lyophilizing the complex. An example of such a folic acid derivative is N-5-methyltetrahydrofolic acid.

15 Claims, No Drawings

STABILIZATION OF SENSITIVE BIOLOGICALLY ACTIVE INTERMEDIATE METABOLITES SUCH AS FOLIC ACID DERIVATIVES

BACKGROUND OF THE INVENTION

Many different chemical substances are metabolized by the human body. Quite often, a number of chemical and/or biochemical reactions take place whereby a parent compound undergoes a plurality of structural changes, with one of the intermediate compounds thereof being a key factor in other but inter-related biochemical pathways. Accordingly, it becomes highly desirable to be able to determine, in a qualitative and/or quantitative fashion, the presence of various metabolic intermediates in a patient's biological fluid sample.

One commonly used approach to qualitatively detect and/or quantitatively measure the presence of a metabolic intermediate is through the use of a competitive protein binding assay. Usually, in order to carry out a competitive binding assay, the intermediate metabolite is obtained from a naturally-occurring source and/or synthesized from a precursor compound and is used in a labeled form for competitive binding to a complementary binder or receptor in competition with the unknown amount of unlabeled intermediate metabolite in the patient's sample. This necessitates an intermediate metabolite characterized by a sufficient degree of stability to be used as an assay reagent, that is, remaining substantially unchanged during a reasonable shelf life, say of at least one week, up to three to four weeks or longer.

As an example of an intermediate metabolite of the type discussed above, there may be mentioned N-5-methyltetrahydrofolic acid, an intermediate metabolite of folic acid. N-5-Methyltetrahydrofolic acid is a component of the blood and important to measure for diagnosing folic acid deficiency. Indeed, in man, folic acid and vitamin $B_{12}$ are metabolically inter-related. It is essential to be able to determine the serum levels of N-5-methyltetrahydrofolic acid and vitamin $B_{12}$ in order to indicate and treat megaloblastic anemia in man. Vitamin $B_{12}$ and folate deficiencies are hematologically and clinically indistinguishable. Quite often, simultaneous assays are carried out for vitamin $B_{12}$ and N-5-methyltetrahydrofolic acid.

The stability problem of N-5-methyltetrahydrofolic acid is exacerbated in the simultaneous vitamin $B_{12}$/folate assay because the preservative favored for stabilizing N-5-methyltetrahydrofolic acid, ascorbic acid, interferes with competitive binding vitamin $B_{12}$ analysis.

The prior art discloses sealing sensitive intermediate metabolites such as N-5-methyltetrahydrofolic acid in lyophilized form in ampoules under a nitrogen atmosphere. Such a technique is very impractical in preparing a reagent kit, plus it would not prolong stability after reconstitution, which for N-5-methyltetrahydrofolic acid is only about three days at 4° C.

SUMMARY OF THE INVENTION

An object of this invention is to provide a process for stabilizing an intermediate metabolite.

Another object of this invention is to provide a process for stabilizing intermediate metabolites in the form of a reagent for a competitive protein binding assay procedure.

Still another object of this invention is to provide a stabilized intermediate metabolite without employing a conventional chemical stabilizer.

A further object of this invention is to provide a competitive binding assay reagent kit, such as a radioassay reagent kit, including intermediate metabolites stabilized in accordance with this invention.

A more specific object of this invention is to provide a process for stabilizing N-5-methyltetrahydrofolic acid and also to provide the resultant stable product.

Other objects of this invention will be apparent to the skilled artisan from the detailed description of the invention hereinbelow.

In accordance with the present invention, an unstable, sensitive intermediate metabolite is stabilized by complexing it with its complementary binder or receptor, preferably a binder or receptor protein. More specifically, in the present invention, the complexation is carried out in a liquid medium and then the mixture is rapidly frozen and dehydrated in the frozen state, il.e., lyophilized. The resultant product is a dry powder.

In a preferred embodiment of the invention, the unstable intermediate metabolite is N-5-methyltetrahydrofolic acid. The N-5-methyltetrahydrofolic acid can be complexed with complementary proteinaceous or non-proteinaceous binder therefor, such as bovine milk binder.

In other preferred embodiments of this invention, the stable complex, in lyophilized form, is a competitive protein binding assay reagent.

DETAILED DESCRIPTION OF THE INVENTION

The present invention will be exemplified with the intermediate metabolite N-5-methyltetrahydrofolic acid. However, it is the inventor's belief that the inventive concept is broader to include other intermediate metabolites and their complementary binders. For example, other folic acid metabolites such as N-10-formyltetrahydrofolic acid, N-5-formiminotetrahydrofolic acid, N-5-formyltetrahydrofolic acid and N-5, N-10-methylenetetrahydrofolic acid; enzymatic substrates; vitamin $B_{12}$; vitamin D; and so on should be substitutable for the N-5-methyltetrahydrofolic acid, with the complementary binding material therefor being known in the art.

For the N-5-methyltetrahydrofolic acid, various folate binder proteins are known, for example, those extracted from various animal organs, particularly kidneys, livers and pancreas, $\beta$-lactoglobulin preparations, dolphin serum, bovine milk, goat milk, and the like.

Although the stability of the intermediate metabolite is increased by complexation per se, the full benefits of the present invention are not realized unless the complex is then frozen and dehydrated to yield a dry powder. More particularly, the intermediate metabolite and binder therefor are admixed in a liquid medium, usually aqueous-based, under conditions to allow the metabolite to bind to its receptor. Such reactions are well known in the biochemical art. Generally, mild incubation conditions are used, say up to about room temperature, although incubation can be carried out from just above the freezing temperature of the mixture up to a temperature below that at which a heat-sensitive binder such as a protein would be destroyed, for a short time, say about 15 minutes to 1 hour. In general, lower temperatures are used with longer time periods.

It is very convenient to carry out the complexation in a liquid medium having a composition similar to or about the same as that in which the complex would be used in reconstituted form at a later date. Thus, various additives such as buffer salts, human serum albumin, other proteins, and the like, which should be present after reconstitution, may be present in the liquid containing the complex as long as these additives do not interfere with complex formation or subsequent lyophilization.

Following a suitable incubation period, the composition is lyophilized in a manner known in the art. The resultant dry powder can be stored in any suitable container, preferably air tight and light resistant. As will be illustrated by examples hereinbelow, storage can be at room temperature or lower. If the complex will not be used for a long period of time, lower temperature storage would be preferable.

For reconstitution, it is only necessary to add the same or different liquid as was used during formation of the complex to the lyophilized dry powder, followed by mixing. For example, a vortex mixer could be used.

Quite often, it is desirable to utilize the intermediate metabolite in its free chemical state, so that it becomes necessary to release the intermediate metabolite from the binder and prevent reformation of the complex. This can be accomplished in a number of different ways. Where a protein binder is used, the simplest release method is to heat the reconstituted material to a temperature and for a time sufficient to destroy the binding protein, say about 95° C. for about 10 to 30 minutes in many cases.

The following examples illustrate the present invention using N-5-methyltetrahydrofolic acid as a representative intermediate metabolite.

EXAMPLE 1

In this example, six pairs of standard value samples of N-5-methyltetrahydrofolic acid containing the concentrations of N-5-methyltetrahydrofolic acid as set forth in Table 1 are used. Each standard value sample is 100 microliters and its composition in addition to the N-5-methyltetrahydrofolic acid is buffer salts, sodium chloride, sodium azide, merthiolate and human serum albumin.

To one member of each pair, there is added the quantity of bovine folate binding protein set forth in Table 1. After admixture, the sample is allowed to incubate at 4° C. for 3 hours. Immediately thereafter, each sample is lyophilized to yield a dry powder. Each sample is reconstituted at day 0 using deionized water and evaluated at day 0, day 4, day 8 and day 14 for the amount of folate present by a radioassay. During the testing period, all reconstituted samples are maintained at 4° C. Day 0 is the day of lyophilization. Using a data reduction technique, the quantity of N-5-methyltetrahydrofolic acid (ng/ml) is determined for each sample. The results are set forth in Table 1.

TABLE 1

| *Nominal Standard Value | **Folate Binding Protein Added | Without Folate Binding Protein Day | | | | With Folate Binding Protein Day | | | |
|---|---|---|---|---|---|---|---|---|---|
| | | 0 | 4 | 8 | 14 | 0 | 4 | 8 | 14 |
| 0 | 0 | −0.08 | −0.06 | 0.06 | — | −0.03 | −0.04 | 0.27 | 0.09 |
| 1 | 3.3 | 0.84 | 0.60 | 0.62 | — | 0.93 | 0.84 | 0.98 | 0.65 |
| 2.5 | 8.3 | 2.1 | 1.9 | 1.5 | — | 2.1 | 2.3 | 2.2 | 2.3 |
| 5.0 | 16.6 | 4.0 | 3.7 | 2.1 | — | 4.4 | 5.2 | 4.5 | 4.2 |
| 10.0 | 33.2 | 8.4 | 8.3 | 6.4 | — | 9.9 | 10.1 | 8.9 | 9.6 |
| 20.0 | 66.4 | 17.9 | 13.8 | 11.7 | — | 21.1 | 17.6 | 17.9 | 21.6 |

*ng/ml of N-5-methyltetrahydrolic acid
**micrograms per ml

EXAMPLE 2

A portion of each of the reconstituted samples of Example 1 was stored at room temperature for 8 days and evaluated as in Example 1. Table 2 sets forth the results. The values at day 0 are, of course, the same as in Example 1.

TABLE 2

| Nominal Standard Value (ng/ml) | Folate Binding Protein Added (mcg/ml) | Without Folate Binding Protein Day | | With Folate Binding Protein Day | |
|---|---|---|---|---|---|
| | | 4 | 8 | 4 | 8 |
| 0 | 0 | −0.10 | 0.28 | −0.01 | 0.24 |
| 1 | 3.3 | 0.30 | 0.30 | 0.66 | 0.87 |
| 2.5 | 8.3 | 0.83 | 0.41 | 2.4 | 2.0 |
| 5.0 | 16.6 | 1.9 | 0.87 | 4.7 | 3.6 |
| 10.0 | 33.2 | 3.4 | 1.3 | 10.1 | 8.4 |
| 20.0 | 66.4 | 6.6 | 2.6 | 18.5 | 18.6 |

EXAMPLE 3

Samples of N-5-methyltetrahydrofolic acid complexed with folate binder protein are prepared as in Example 1 and stored after reconstitution at 4° C. The concentration of N-5-methyltetrahydrofolic acid therein is determined as in Example 1 but after 0, 2, 3, 4, 5, 6, 7 and 8 weeks. The results are set forth in Table 3.

TABLE 3

| Nominal Standard Value (ng/ml) | Weeks at 4° C. | | | | | | | |
|---|---|---|---|---|---|---|---|---|
| | 0 | 2 | 3 | 4 | 5 | 6 | 7 | 8 |
| 1.0 | 1.7 | 1.5 | 1.3 | 1.3 | 1.2 | 1.0 | 1.1 | 0.8 |
| 2.5 | 3.1 | 3.0 | 2.8 | 2.5 | 2.2 | 1.9 | 2.3 | 2.0 |
| 5.0 | 6.6 | 5.9 | 5.7 | 5.7 | 4.7 | 5.0 | 5.5 | 5.7 |
| 10.0 | 11.8 | 10.9 | 9.9 | 9.8 | 8.9 | 9.1 | 10.1 | 11.1 |
| 20.0 | 20.6 | 20.1 | 20.4 | 20.3 | — | 20.9 | 18.4 | 19.7 |

EXAMPLE 4

A series of lyophilized samples as used in Example 3 is stored at about 4° C. and reconstituted on the day of analysis. Measurements are taken at weeks 5, 6, 7 and 8 with the results thereof being set forth in Table 4.

TABLE 4

| Freshly reconstituted | Weeks at 4° C. | | | |
|---|---|---|---|---|
| | 5 | 6 | 7 | 8 |
| 1.0 | 1.2 | 1.3 | 1.5 | 1.1 |
| 2.5 | 2.7 | 2.7 | 2.7 | 2.9 |

TABLE 4-continued

| Freshly reconstituted | Weeks at 4° C. | | | |
| --- | --- | --- | --- | --- |
|  | 5 | 6 | 7 | 8 |
| 5.0 | 4.2 | 6.1 | 5.6 | 5.8 |
| 10 | — | 11.5 | 11.4 | 11.4 |
| 20 | — | 22.7 | 19.1 | 18.4 |

Variations of the invention will be apparent to the skilled artisan. For example, from a generic viewpoint, the receptor could be non-proteinaceous, such as an ion exchange resin, a column of hydrophobic material, or the like to which small molecules can bind. Also, in vitro experiments have shown that glass particles are capable of mimicking protein receptor surfaces. At times, although the receptor is a protein, the binding occurs through a non-proteinaceous portion of the protein, such as included carbohydrate, lipid and/or peptide moieties.

What is claimed is:

1. A method for stabilizing an intermediate metabolite which is a folic acid derivative or analog, which method comprises complexing said intermediate metabolite in a liquid medium with a complementary binder or receptor therefor and then lyophilizing said complex to yield a dry powder containing said stable complex.

2. The method of claim 1 wherein the binder or receptor is a protein.

3. The method of claim 2 wherein said intermediate metabolite is in an aqueous-based liquid, said binder or receptor protein is admixed therewith and the mixture is incubated at a temperature from just above the freezing temperature of the mixture up to but not including the temperature at which the binder or receptor protein would be destroyed for a time sufficient to form said complex prior to said lyophilization.

4. The method of claim 1 or claim 3 wherein the intermediate metabolite is N-5-methyltetrahydrofolic acid.

5. The method of claim 1 or claim 3 wherein said liquid includes at least one additional ingredient desired to be present when the lyophilized material is reconstituted for use.

6. The method of claim 5 wherein the intermediate metabolite is N-5-methyltetrahydrofolic acid.

7. A stable complex of an intermediate metabolite complexed with a binder or receptor therefor in lyophilized dry powder form, which intermediate metabolite is a folic acid derivative or analog.

8. The complex of claim 7 wherein the binder or receptor is a protein.

9. The complex of claim 7 or claim 8 prepared by the process of any of claims 1 or 3.

10. A competitive protein binding assay reagent kit including the complex of claim 9.

11. The complex of claim 9 wherein the intermediate metabolite is N-5-methyltetrahydrofolic acid.

12. A competitive protein binding assay reagent kit including the complex of claim 11.

13. The complex of claim 7 or claim 8 wherein the intermediate metabolite is N-5-methyltetrahydrofolic acid.

14. A competitive protein binding assay reagent kit including the complex of claim 13.

15. A competitive protein binding assay reagent kit including the complex of claim 7 or claim 10.

* * * * *